United States Patent
Mower

(10) Patent No.: US 6,411,845 B1
(45) Date of Patent: *Jun. 25, 2002

(54) SYSTEM FOR MULTIPLE SITE BIPHASIC STIMULATION TO REVERT VENTRICULAR ARRHYTHMIAS

(75) Inventor: Morton M. Mower, Baltimore, MD (US)

(73) Assignee: Mower CHF Treatment Irrevocable Trust, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/654,995

(22) Filed: Sep. 5, 2000

Related U.S. Application Data

(62) Division of application No. PCT/US99/04695, filed on Mar. 4, 1999.

(51) Int. Cl.[7] .................................................. A61N 1/39
(52) U.S. Cl. ......................................................... 607/5
(58) Field of Search ............................... 607/4, 5, 14, 6, 607/7, 8, 9

(56) References Cited

U.S. PATENT DOCUMENTS

| | | |
|---|---|---|
| 3,924,641 A | 12/1975 | Weiss |
| 3,946,745 A | 3/1976 | Hiang-Lai et al. |
| 4,019,519 A | 4/1977 | Geerling |
| 4,055,190 A | 10/1977 | Tany |
| 4,222,386 A | 9/1980 | Smolnikov et al. ............ 607/9 |
| 4,233,986 A | 11/1980 | Tannenbaum |
| 4,298,007 A | 11/1981 | Wright et al. |
| 4,327,322 A | 4/1982 | Yukl |
| 4,343,312 A | 8/1982 | Cals et al. .................. 128/419 |
| 4,392,496 A | 7/1983 | Stanton |
| 4,402,322 A | 9/1983 | Duggan |
| 4,429,697 A | 2/1984 | Nappholz et al. |

(List continued on next page.)

FOREIGN PATENT DOCUMENTS

| | | |
|---|---|---|
| EP | 0491649 A2 | 6/1992 |
| EP | 0600631 A2 | 11/1993 |
| EP | 0 491 649 B1 | 9/1996 |
| EP | 0 813 889 A2 | 12/1997 |
| EP | 0 850 662 | 7/1998 |
| EP | 0 870 516 | 10/1998 |
| EP | 0 600 631 | 12/1999 |
| FR | 2763247 | 11/1998 |
| WO | 93/01861 | 2/1993 |
| WO | 97/25098 | 7/1997 |

*Primary Examiner*—Scott M. Getzow
(74) *Attorney, Agent, or Firm*—Roberts Abokhair & Mardula, LLC

(57) ABSTRACT

An anti-reentry apparatus and method for reverting ventricular arrhythmias. Biphasic stimulation is applied at multiple ventricular sites to revert arrhythmias caused by reentry, particularly multiple random reentry. In the preferred embodiment, the first phase of biphasic stimulation is anodal, and is at a maximum subthreshold amplitude. The anodal phase preconditions the myocardium to accept the second phase (cathodal) such that less electrical energy is required to reach the threshold amplitude to produce depolarization. The anodal phase stimulation may have a shape over time that is square wave, ramped, or a series of short square wave pulses. Multiple electrodes located at multiple ventricular sites may be stimulated simultaneously, or they may be sequentially stimulated over time in a manner mimicking the normal progress pattern of cardiac depolarization. The multiple ventricular electrodes may stimulate from internal or external surfaces. One or both ventricles may receive biphasic stimulation from multiple electrodes. The invention also may be practiced with respect to atria.

22 Claims, 3 Drawing Sheets

U.S. PATENT DOCUMENTS

| | | |
|---|---|---|
| 4,444,195 A | 4/1984 | Gold |
| 4,456,012 A | 6/1984 | Lattin |
| 4,498,478 A | 2/1985 | Bourgeois |
| 4,539,991 A | 9/1985 | Boute et al. |
| 4,543,956 A | 10/1985 | Herscovoci |
| 4,569,350 A | 2/1986 | Mumford et al. |
| RE32,091 E | 3/1986 | Stanton |
| 4,612,934 A | 9/1986 | Borkan |
| 4,637,397 A | 1/1987 | Jones et al. ............... 128/419 |
| 4,646,744 A | 3/1987 | Capel |
| 4,723,552 A | 2/1988 | Kenyon et al. |
| 4,754,759 A | 7/1988 | Allocca |
| 4,781,194 A | 11/1988 | Elmqvist |
| 4,821,724 A | 4/1989 | Whigham et al. ............ 607/13 |
| 4,823,810 A | 4/1989 | Dervieux |
| 4,875,484 A | 10/1989 | Anzai et al. |
| 4,903,700 A | 2/1990 | Whigham et al. .......... 128/419 |
| 4,919,140 A | 4/1990 | Borgens et al. |
| 4,924,880 A | 5/1990 | O'Neill et al. |
| 4,940,054 A | 7/1990 | Grevis et al. |
| 4,944,298 A | 7/1990 | Sholder |
| 4,976,264 A | 12/1990 | Petrofsky |
| 4,989,605 A | 2/1991 | Rossen |
| 4,996,987 A | 3/1991 | Petrofsky |
| 5,018,522 A | 5/1991 | Mehra ......................... 607/10 |
| 5,027,815 A | 7/1991 | Funke et al. |
| 5,036,850 A | 8/1991 | Owens |
| 5,048,522 A | 9/1991 | Petrofsky |
| 5,052,391 A | 10/1991 | Silberstone et al. |
| 5,058,584 A | 10/1991 | Bourgeois |
| 5,063,929 A | 11/1991 | Bartelt et al. |
| 5,065,083 A | 11/1991 | Owens |
| 5,069,211 A | 12/1991 | Bartelt et al. |
| 5,083,564 A | 1/1992 | Scherlag |
| 5,097,833 A | 3/1992 | Campos |
| 5,105,810 A | 4/1992 | Collins et al. |
| 5,109,847 A | 5/1992 | Liss et al. |
| 5,111,811 A | 5/1992 | Smits |
| 5,117,826 A | 6/1992 | Bartelt et al. |
| 5,163,429 A | 11/1992 | Cohen |
| 5,181,511 A | 1/1993 | Nickolls et al. |
| 5,193,535 A | 3/1993 | Bardy et al. |
| 5,209,229 A | 5/1993 | Gilli |
| 5,213,098 A | 5/1993 | Bennett et al. |
| 5,215,083 A | 6/1993 | Drane et al. |
| 5,224,475 A | 7/1993 | Berg et al. |
| 5,224,476 A | 7/1993 | Ideker et al. ............... 128/419 |
| 5,233,985 A | 8/1993 | Hudrlik |
| 5,300,096 A | 4/1994 | Hall et al. ..................... 607/48 |
| 5,314,423 A | 5/1994 | Seney ........................... 606/20 |
| 5,314,495 A | 5/1994 | Kovacs ......................... 623/25 |
| 5,332,401 A | 7/1994 | Davey et al. ............... 607/116 |
| 5,334,220 A | 8/1994 | Sholder |
| 5,340,361 A | 8/1994 | Sholder |
| 5,350,401 A | 9/1994 | Levine |
| 5,391,185 A | 2/1995 | Kroll ............................. 607/4 |
| 5,411,525 A | 5/1995 | Swanson et al. ............... 607/5 |
| 5,411,547 A | 5/1995 | Causey, III ................. 607/129 |
| 5,421,830 A | 6/1995 | Epstein et al. ................ 607/30 |
| 5,422,525 A | 6/1995 | Mansir |
| 5,423,868 A | 6/1995 | Nappholz et al. |
| 5,441,522 A | 8/1995 | Schuller |
| 5,458,625 A | 10/1995 | Kendall ........................ 607/46 |
| 5,468,254 A | 11/1995 | Hahn et al. .................... 607/5 |
| 5,480,413 A | 1/1996 | Greenhut et al. ............. 607/14 |
| 5,487,759 A | 1/1996 | Bastyr et al. ............... 607/149 |
| 5,507,781 A | 4/1996 | Kroll et al. .................... 607/7 |
| 5,514,161 A | 5/1996 | Limousin ....................... 607/9 |
| 5,514,163 A | 5/1996 | Markowitz et al. |
| 5,522,858 A | 6/1996 | van der Veen ............... 607/14 |
| 5,527,347 A | 6/1996 | Shelton et al. |
| 5,534,015 A | 7/1996 | Kroll et al. .................... 607/7 |
| 5,534,018 A | 7/1996 | Wahlstrand et al. .......... 607/27 |
| 5,545,186 A | 8/1996 | Olson et al. |
| 5,562,708 A | 10/1996 | Combs et al. ................. 607/4 |
| 5,601,608 A | 2/1997 | Mouchawar ................... 607/5 |
| 5,620,470 A | 4/1997 | Gliner et al. .................. 607/5 |
| 5,620,471 A | 4/1997 | Duncan ....................... 607/14 |
| 5,626,620 A | 5/1997 | Kieval et al. |
| 5,649,966 A | 7/1997 | Noren et al. ................... 607/4 |
| 5,662,698 A | 9/1997 | Altman et al. ............. 607/123 |
| 5,713,929 A | 2/1998 | Hess et al. ................... 607/14 |
| 5,718,720 A | 2/1998 | Prutchi et al. |
| 5,735,876 A | 4/1998 | Kroll et al. |
| 5,741,303 A | 4/1998 | Kroll et al. .................... 607/5 |
| 5,800,465 A | 9/1998 | Thompson et al. ............ 607/9 |
| 5,814,079 A | 9/1998 | Kieval ........................... 607/4 |
| 5,855,592 A | 1/1999 | McGee et al. |
| 5,855,594 A | 1/1999 | Olive et al. |
| 5,871,506 A | 2/1999 | Mower ........................... 607/9 |
| 5,968,081 A | 10/1999 | Levine ........................... 607/9 |
| 6,067,470 A * | 5/2000 | Mower |
| 6,136,019 A | 10/2000 | Mower ........................... 607/9 |
| 6,141,586 A | 10/2000 | Mower ........................... 607/9 |
| 6,141,587 A | 10/2000 | Mower ........................... 607/9 |
| 6,178,351 B1 | 1/2001 | Mower ........................... 607/5 |

* cited by examiner

SYSTEM FOR MULTIPLE SITE BIPHASIC STIMULATION TO REVERT VENTRICULAR ARRHYTHMIAS

CROSS REFERENCE TO RELATED APPLICATIONS

This application is a divisional of PCT application no. PCT/US 99/04695, filed Mar. 4, 1999, pending, which claims priority from U.S. patent application Ser. No. 09/035,455, filed Mar. 5, 1998, now U.S. Pat. No. 6,067,470. The PCT application Ser. No. PCT/US 99/04695, application Ser. No. 09/035,455, and U.S. Pat. No. 6,067,470 are each incorporated by reference herein, in their entirety, for all purposes.

BACKGROUND OF THE INVENTION

1. Field of the Invention

The present invention relates generally to an anti-reentry apparatus and method that can favorably influence the beating of ineffective hearts, especially hearts with pathological conditions that interfere with normal rhythmicity, electrical conduction, and/or contractility by causing ventricular fibrillation. The present invention particularly relates to an anti-reentry apparatus and method that provides simultaneous or progressive biphasic stimulation at multiple sites in one or both ventricles.

2. Background Information

Heart disease and malfunction is a major killer of men and women in America. A variety of pathologies can affect the beating patterns of a heart, and thereby predispose it to developing ventricular fibrillation. Prior to the occurrence of such a severe and ineffective rhythm, conventional pacemakers can be used to treat, for example, such disorders as sino-atrial (SA) node block, A-V block, and multiple independent sites of contraction in the ventricles (also termed ectopic foci), which, in the extreme, can lead to life threatening ventricular fibrillation. Conventional pacemakers often will control and prevent the recurrence of ectopic foci by preprogrammed stimulation of (usually) the right ventricle via a single electrode. Some pacemakers also employ a second electrode that is dedicated to the left ventricle. In addition, conventional pacemakers utilize a range of circuit logic patterns to counter specific problems that are encountered in the more common pathologies.

However, conventional single ventricular electrode technologies, including the use of a separate single electrode to each ventricle, fail in cases in which ventricular fibrillation has ensued (particularly when the fibrillation is due to multiple random reentry), and single site stimulation does not entrain sufficiently large areas of surrounding tissue to produce the concerted contraction that is necessary for optimal efficiency in pumping blood. In such cases of ventricular fibrillation from multiple random reentry, the patient is put in grave jeopardy for the basic reason that virtually all of the body functions depend on delivery of blood to the tissues in order to supply oxygen and nutrients, and also to carry away metabolic waste products. Failure to correct such a condition, where the rhythm is so far from optimal, results in the patient being in substantial danger of dying in a very short period of time. Though cardioversion/defibrillation may be employed, including that preprogrammed in the control logic for automatic activation in some pacemaker-defibrillators, such protocols typically require large doses of electrical energy to the patient. In addition to producing extreme discomfort and sharp pain, these large doses of electrical energy often also produce cardiac damage. The voltage for standard internal defibrillation/cardioversion is from 150 to 800 volts, corresponding to approximately 10–35 joules.

Several approaches to these problems have been disclosed. One approach is to stimulate greater portions of ventricular myocardium by utilizing larger electrodes so that greater portions of myocardium are simultaneously stimulated. For example, U.S. Pat. No. 5,411,547 to Causey, III discloses the use of defibrillation electrode patches for more efficient bipolar cardiac stimulation. In addition, the use of large, plate-like electrodes for defibrillation and cardioversion is well known. However, the use of such larger electrodes suffers from the problem of delivery of large doses of electrical energy that produce great discomfort to the patient and the possibility of tissue damage.

Yet another approach is to use multiple individual electrodes appropriately placed about the ventricles. For further details, refer to the following U.S. Pat. Nos. 5,649,966 to Noren et al., 5,391,185 to Kroll, 5,224,475 to Berg et al., 5,181,511 to Nickolls et al., and 5,111,811 to Smits. Though these patents disclose the use of multiple electrodes, they do not disclose or suggest their use for gradually (yet quickly) entraining the various reentrant foci that can exist in pathological ventricles by stimulating in a progressive pattern that mimics the normal wave of depolarization that occurs in the heart.

Thus, a need exists for an anti-reentry apparatus and method that will require the use of less electrical current/voltage than is typically used for defibrillation and cardioversion in order to decrease the likelihood, or at least the severity, of tissue damage. A need also exists for an anti-reentry apparatus and method that will simultaneously stimulate greater portions of ventricular myocardium to increase the probability of ventricular conversion (particularly in the presence of multiple random reentry), but with delivery of lower doses of electrical energy per stimulation, which, consequently, will prolong the life of the apparatus's batteries and decrease myocardial soft tissue damage. A need also exists for such an anti-reentry apparatus and method that not only will produce the vitally needed improvement in cardiac pumping efficiency, but additionally will simultaneously lower the probability of tissue damage, and provide greater comfort for the patient. In addition, a need exists for an anti-reentry apparatus and method that progressively stimulates the ventricles in a manner that mimics the normal cardiac wave of depolarization, thereby providing rapid control and reversion of cardiac rhythm to a normal beating pattern.

SUMMARY OF THE INVENTION

In view of the foregoing limitations in the art, it therefore is an object of the present invention to provide an apparatus and method that more efficiently and quickly entrains larger areas of myocardium to promote ventricular conversion, particularly in patients suffering from episodes of multiple random ventricular reentrant foci that produce, or may produce, ventricular fibrillation.

It is another object of the present invention to provide an apparatus and method that, while entraining larger areas of myocardium, does so with smaller doses of electrical energy than typically are used in defibrillation and cardioversion.

It is yet another object of the present invention to provide an apparatus and method that, while entraining larger areas of myocardium, does so by stimulating in a progressive pattern that mimics the normal wave of depolarization of the heart.

It is a further object of the present invention to provide an apparatus and method that, while entraining larger areas of myocardium, does so with less stress on the heart and greater comfort to the patient.

It is yet another object of the present invention to provide an apparatus and method that, while entraining larger areas of myocardium, does so with less damage to cardiac tissue.

It is yet a further object of the present invention to provide an apparatus and method that, while entraining larger areas of myocardium, also promotes greater myocardial blood pumping efficiency.

It is yet a further object of the present invention to provide an apparatus and method that entrains larger areas of myocardium by using multiple electrodes that provide biphasic stimulation.

Pacemakers, which utilize low energy stimulation pulses, constitute a separate and distinct art from cardioverters/defibrillators, which utilize stimulation pulses of much larger energy—even when the electrodes are positioned directly on the heart. Thus, according to conventional practice, more energy is required to entrain the entire heart (cardioversion/defibrillation) than to exogenously employ the traditional pacemaker that typically utilizes the natural cardiac conducting fibers and/or endogenous pacemaker(s) to control the beating of a heart that is only slightly "out of synch" relative to the more dangerous rhythmicity disorders that often result in extensive fibrillation.

An intermediate ground is demonstrated by the present invention. By using multiple electrodes and applying biphasic stimulation, one or both ventricles may gradually (yet quickly) be entrained to beat more normally in the face of multiple random reentry, even though the stimulation energy level used is lower than that generally used for cardioversion/defibrillation.

Thus, the present invention accomplishes the above objectives by utilizing multiple electrodes that contact multiple ventricular areas 1) for simultaneous biphasic stimulation, or 2) for progressive biphasic stimulation, that is, the mimicking of the physiological patterns of electrical current flows or waves of depolarization in the myocardium. The control circuit logic can activate the multiple site, biphasic ventricular stimulation upon the occurrence of A-V block in a patient known to be susceptible to multiple random ventricular reentrant foci, or upon the direct or indirect sensing of ventricular fibrillation. For example, direct sensing of ventricular fibrillation can be based on data from multiple ventricular sensing electrodes, and indirect sensing can be based on any of various functional parameters, such as arterial blood pressure, size and/or presence of an R wave, rate of the electrogram deflections, or the probability density function (PDF) of the electrogram.

The present invention accomplishes the above objectives through the use of multiple site, biphasic ventricular stimulation in one or both ventricles to 1) gradually (yet quickly) entrain and interrupt substantially all of the multiple random reentrant circuits that are present; or, failing that, 2) reduce the number of such reentrant circuits to a level at which much smaller stimuli may be used than in conventional defibrillation/cardioversion to convert the rhythms to more normal ones, and thereby produce coordinated and efficient cardiac function.

The first and second phases of stimulation consist of an anodal pulse (first phase) followed by a cathodal pulse (second phase). In a preferred embodiment, the first phase of stimulation is an anodal pulse at maximum subthreshold amplitude and for a long duration in order to precondition the myocardium for subsequent stimulation, and the second phase of stimulation is a cathodal pulse with a short duration and a high amplitude. Additional embodiments of the first phase include, but are not limited to, the use of ramped pulses, a series of short duration square wave pulses, anodal pulses that are less than the maximum subthreshold amplitude, and pulses whose magnitudes decay from an initial subthreshold amplitude to a lower amplitude, where the shape of the decay can be linear or curvilinear. It is to be understood that the use of the phrase "medium energy" stimulation or pulse refers to electrical stimulation or electrical pulses in which the magnitude of the voltage of the electrical stimulation/pulse is lower in magnitude than that used in typical defibrillation/cardioversion.

BRIEF DESCRIPTION OF THE DRAWINGS

FIG. 1-B depicts a heart with multiple ventricular electrodes that are connected to external surfaces of the ventricles, and include a separate electrode set each for the right and left ventricles.

DETAILED DESCRIPTION OF THE INVENTION

Figure 1A:
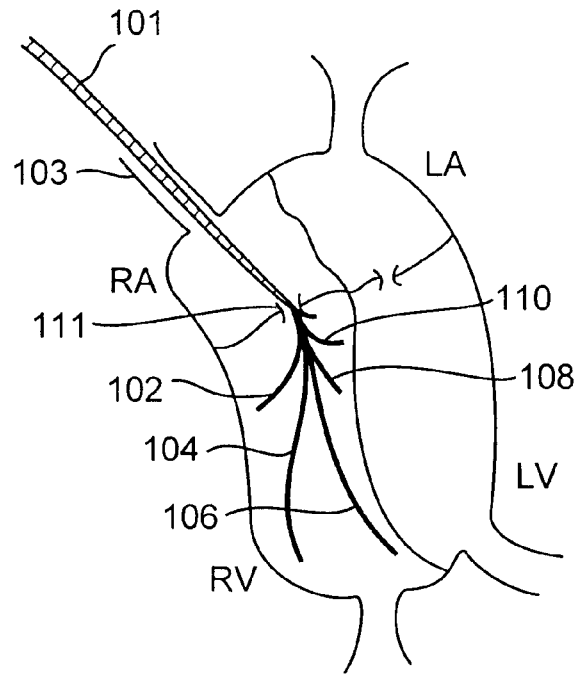
FIG. 1-A depicts a heart with multiple ventricular electrodes that are introduced via the vena cava.
Figure 1B:
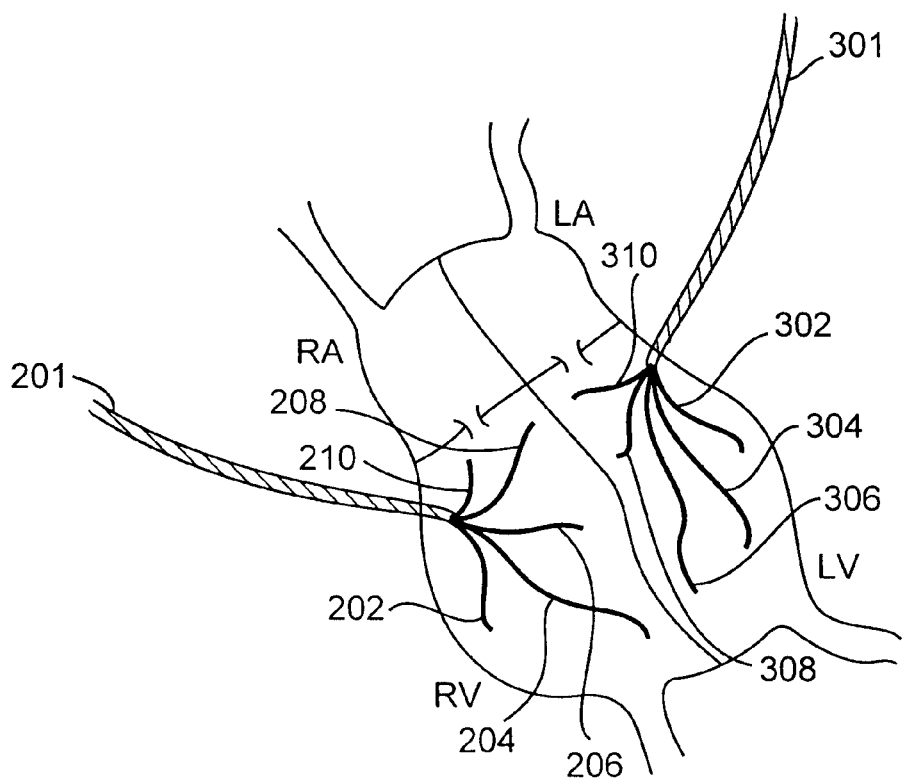

The apparatus and method of the present invention may be understood with reference to FIGS. 1-A, 1-B, and 2 to 5.

Referring to FIG. 1-A, a diagram of the heart is shown connected to vena cava 103, and having four chambers: right atrium (RA), left atrium (LA), right ventricle (RV), and left ventricle (LV). Electrode lead 101 is shown feeding into the right ventricle via vena cava 103, the right atrium, and tricuspid valve 111. Individual electrodes 102, 104, 106, 108 and 110 are connected to electrode lead 101, and contact multiple internal sites of the right ventricle. No set number, or absolute range as to the number, of individual electrodes is required to practice this embodiment of the present invention. A typical range could encompass 2 to 30 electrodes, though numbers greater than 30 are also contemplated. In addition, there is no set placement of these electrodes. In a preferred embodiment, 6 or less electrodes are used, 4 in the left ventricle and 2 in the right ventricle. It is noted that stimulation of the atria through the practice of the present invention also is envisioned.

Referring to FIG. 1-B, a similar diagram of the heart is shown in which two sets of multiple electrodes are depicted connected to external ventricular surfaces. Electrode lead 201, connected to individual electrodes 202, 204, 206, 208 and 210, is shown with the individual electrodes connected to multiple points on the external surfaces of the right ventricle. Electrode lead 301, connected to individual electrodes 302, 304, 306, 308 and 310, is shown with the individual electrodes connected to multiple points on the external surfaces of the left ventricle.

In alternative embodiments, the locations of the individual electrodes in FIG. 1-A (102, 104, 106, 108 and 110), and in FIG. 1-B (202, 204, 206, 208 and 210; and 302, 304, 306, 308 and 310) may 1) follow a regular or relatively regular geometric pattern (e.g., an orthogonal or other patterned grid) so as to cover well the ventricular surfaces in appropriate locations; 2) be localized to a particular ventricular area that is known or suspected to be a source of random reentry circuits; 3) be randomly placed about the selected ventricular surfaces; and/or 4) be placed about the ventricular surfaces in a progressive pattern to facilitate mimicking the normal physiological flow of the depolarization wave that leads to the most efficient contraction of the particular ventricle(s).

The latter progressive stimulation embodiment, which mimics the normal physiological flow of the normal ventricular depolarization wave, requires that areas closest to (or at) the A-V node be the areas first stimulated during a given beat, and that areas farthest from the A-V node—following the normal intrinsic conduction paths—be the last areas to be stimulated. Areas intermediate between these two extremes are appropriately stimulated on a scaled time basis that, again, mimics the normal intrinsic conduction paths that facilitate the most efficient cardiac contraction.

This progressive stimulation embodiment requires specific knowledge of the placement of each electrode relative to each other electrode, as well as the placement relative to the electrical conduction pathways in the heart. Thus, it is appropriate to contemplate "classes" of electrodes, in which, for example, electrodes are identified or categorized according to when they are fired. In a simplistic five tier system, e.g., the first tier electrodes are designated as the first to be fired (i.e., the electrodes closest to the A-V node), followed successively (and temporally progressively according to the normal conducting paths) by the second, third, fourth, and fifth tier electrodes, where the fifth tier electrodes would be the last to be fired, and whose locations on the ventricle(s) would correspond to the last areas to be depolarized in the course of a normal ventricular contraction/beat. An even simpler (i.e., two, three or four) tiered system may be used, or one more complex (i.e., one with greater than 5 tiers, or with any other basis of electrode placement, such as a honeycomb-like array in a particular area with a known or suspected pathology as to rhythmicity, reentry, conduction, contractility, etc.). Furthermore, multiple electrodes within a given tier may be numbered or otherwise distinctly identified so that the practitioner may test and use electrodes with respect to known locations in the heart, for example, to anticipate and/or bypass an area of electrical blockage. This type of embodiment would require the use of multiple, small electrodes pulsed in a physiologic sequential fashion. In application to atria, electrodes are progressively placed from close to the SA node (first to be fired) to close to the AV node (last to be fired), mimicking the normal intrinsic conduction paths.

Bypassing an area of electrical blockage is also anticipated by the present invention, and can be effected by first identifying such areas, for example, by determining myocardial resistance values between electrodes. Electrical pulses then are routed to those myocardial areas with appropriately low resistances, following as closely as possible the lines of conduction of the normal intrinsic conduction paths. Communication of, and control of, measurements of resistance between electrodes, as well as developing a bypass protocol for a particular patient, can be effected by an external computer. The external computer can communicate with the pacemaker by any convenient method, for example, radiotelemetry, direct coupling (as by connecting to an external wire from the pacemaker to the surface of the skin of the patient), etc.

FIGS. 2 through 5 depict a range of biphasic stimulation protocols. These protocols have been disclosed in U.S. patent application Ser. No. 08/699,552 (filed Aug. 19, 1996 by the inventor of the present application), which is incorporated by reference herein, in its entirety, for all purposes.

Figure 2:
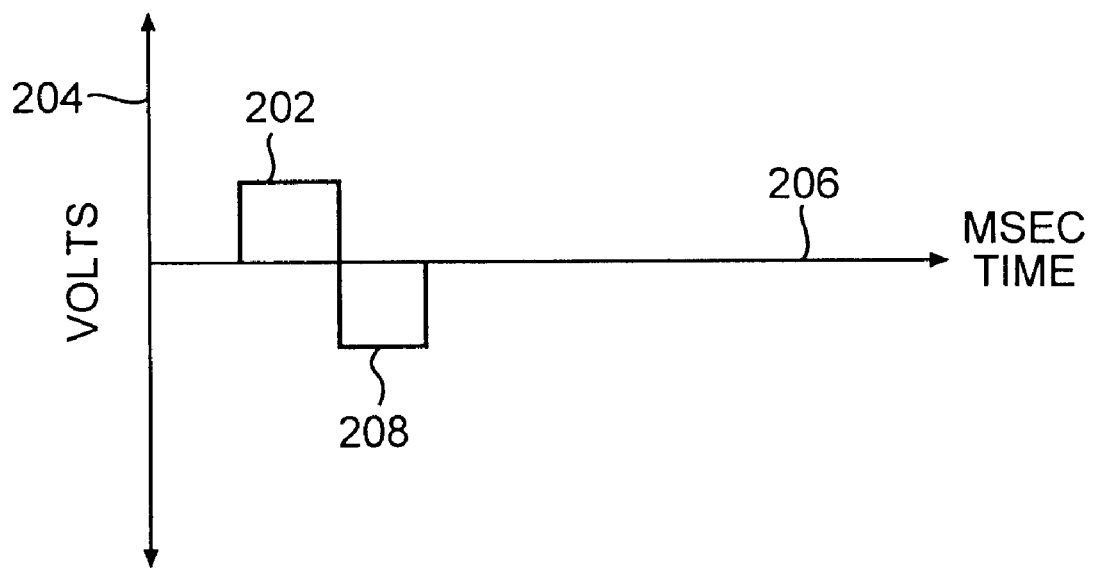
FIG. 2 is a schematic representation of leading anodal biphasic stimulation.

FIG. 2 depicts biphasic electrical stimulation in which a first stimulation phase comprising anodal stimulus 202 is administered with amplitude 204 and duration 206. The first stimulation phase is followed immediately by a second stimulation phase comprising cathodal stimulus 208, which is of equal intensity and duration to those of anodal stimulus 202.

Figure 3:
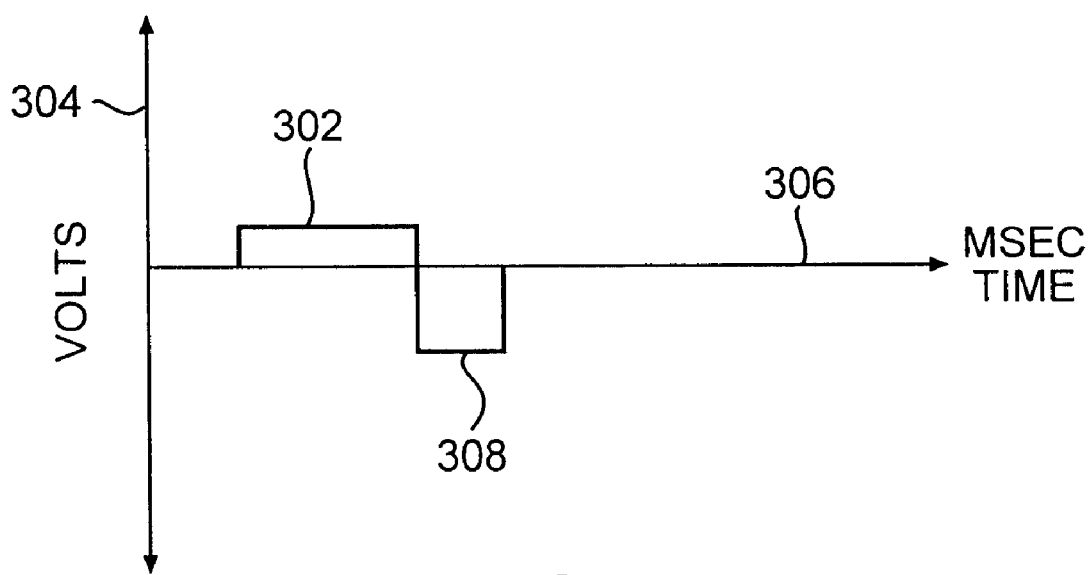
FIG. 3 is a schematic representation of leading anodal stimulation of low level and long duration, followed by cathodal stimulation.

FIG. 3 depicts biphasic electrical stimulation wherein a first stimulation phase comprising low level, long duration anodal stimulation 302 having amplitude 304 and duration 306 is administered. This first stimulation phase is immediately followed by a second stimulation phase comprising cathodal stimulation 308 of conventional intensity and duration. In an alternative embodiment of the invention, anodal stimulation 302 is at maximum subthreshold amplitude. In yet another alternative embodiment of the invention, anodal stimulation 302 is less than three volts. In another alternative embodiment of the invention, anodal stimulation 302 is a duration of approximately two to eight milliseconds. In yet another alternative embodiment of the invention, cathodal stimulation 308 is of a short duration. In another alternative embodiment of the invention, cathodal stimulation 308 is approximately 0.3 to 1.5 milliseconds. In yet another alternative embodiment of the invention, cathodal stimulation 308 is of a high amplitude. In another alternative embodiment of the invention, cathodal stimulation 308 is in the approximate range of three to twenty volts. In yet another alternative embodiment of the present invention, cathodal stimulation 308 is of a duration less than 0.3 milliseconds and at a voltage greater than twenty volts. In another alternative embodiment, anodal stimulation 302 is administered over 200 milliseconds post heart beat. In the manner disclosed by these embodiments, as well as those alterations and modifications which may become obvious upon the reading of this specification, a maximum membrane potential without activation is achieved in the first phase of stimulation.

Figure 4:
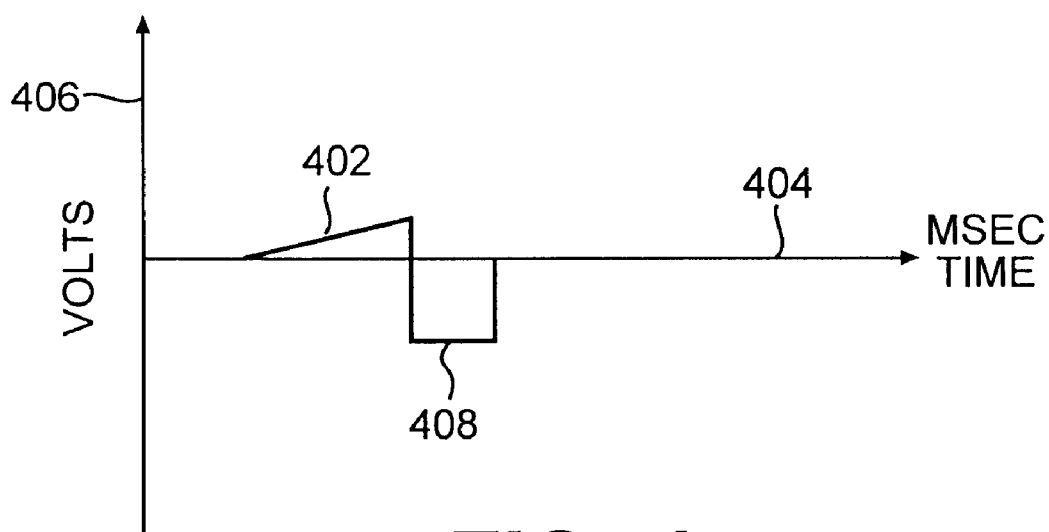
FIG. 4 is a schematic representation of leading anodal stimulation of ramped low level and long duration, followed by cathodal stimulation.

FIG. 4 depicts biphasic electrical stimulation wherein a first stimulation phase comprising anodal stimulation 402 is administered over period 404 with rising intensity level 406. The ramp of rising intensity level 406 may be linear or non-linear, and the slope may vary. This anodal stimulation is immediately followed by a second stimulation phase comprising cathodal stimulation 408 of conventional intensity and duration. In an alternative embodiment of the invention, anodal stimulation 402 rises to a maximum subthreshold amplitude. In yet another alternative embodiment of the invention, anodal stimulation 402 rises to a maximum amplitude that is less than three volts. In another alternative embodiment of the invention, anodal stimulation 402 is a duration of approximately two to eight milliseconds. In yet another alternative embodiment of the invention, cathodal stimulation 408 is of a short duration. In another alternative embodiment of the invention, cathodal stimulation 408 is approximately 0.3 to 1.5 milliseconds. In yet another alternative embodiment of the invention, cathodal stimulation 408 is of a high amplitude. In another alternative embodiment of the invention, cathodal stimulation 408 is in the approximate range of three to twenty volts. In yet another alternative embodiment of the present invention, cathodal stimulation 408 is of a duration less than 0.3 milliseconds and at a voltage greater than twenty volts. In another alternative embodiment, anodal stimulation 402 is administered over 200 milliseconds post heart beat. In the manner disclosed by these embodiments as well as those alterations and modifications which may become obvious upon the reading of this specification, a maximum membrane potential without activation is achieved in the first phase of stimulation.

Figure 5:
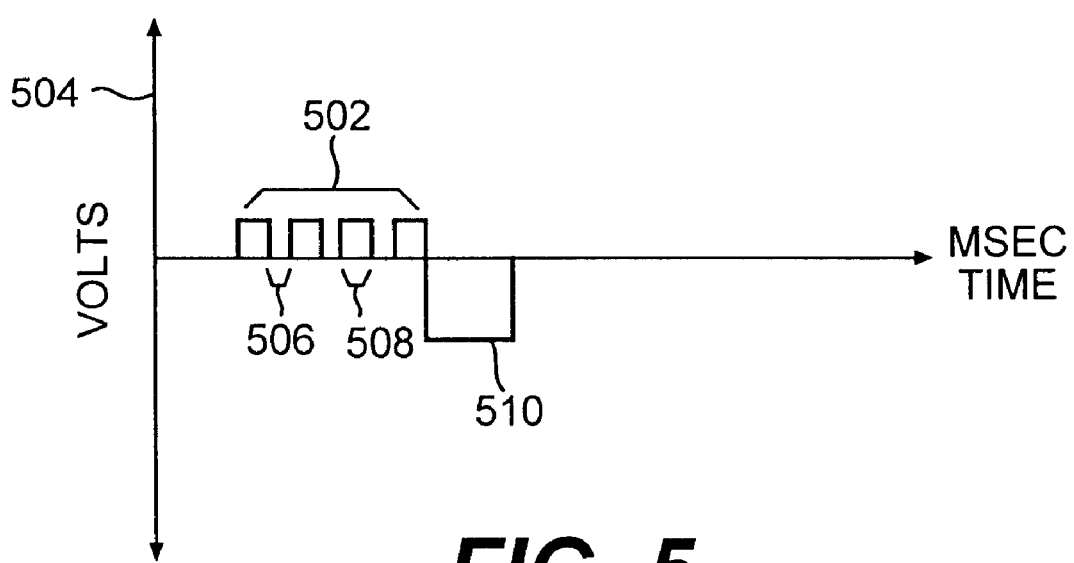
FIG. 5 is a schematic representation of leading anodal stimulation of low level and short duration administered in a series, followed by cathodal stimulation.

FIG. 5 depicts biphasic electrical stimulation wherein a first stimulation phase comprising series 502 of anodal pulses is administered at amplitude 504. In one embodiment rest period 506 is of equal duration to stimulation period 508 and is administered at baseline amplitude. In an alternative embodiment, rest period 506 is of a differing duration than stimulation period 508 and is administered at baseline amplitude. Rest period 506 occurs after each stimulation period 508 with the exception that a second stimulation phase comprising cathodal stimulation 510 of conventional intensity and duration immediately follows the completion of series 502. In an alternative embodiment of the invention, the total charge transferred through series 502 of anodal stimulation is at the maximum subthreshold level. In yet another alternative embodiment of the invention, the first stimulation pulse of series 502 is administered over 200 milliseconds post heart beat. In another alternative embodiment of the invention, cathodal stimulation 510 is of a short duration. In yet another alternative embodiment of the invention, cathodal stimulation 510 is approximately 0.3 to 1.5 milliseconds. In another alternative embodiment of the invention, cathodal stimulation 510 is of a high amplitude. In yet another alternative embodiment of the invention, cathodal stimulation 510 is in the approximate range of three to twenty volts. In another alternative embodiment of the invention, cathodal stimulation 510 is of a duration less than 0.3 milliseconds and at a voltage greater than twenty volts. The individual pulses of the series of pulses may be square waves, or they may be of any other shape, for example, pulses which decay linearly or curvilinearly from an initial subthreshold amplitude, to a lower amplitude.

In the preferred biphasic stimulation protocol practiced by the present invention, the magnitude of the anodal phase does not exceed the maximum subthreshold amplitude. The anodal phase serves to precondition the stimulated myocardium, thereby lowering the excitation threshold such that a cathodal stimulation of lesser intensity than normal will produce depolarization leading to contraction.

The values of duration and amplitude will depend on factors such as the placement/position of the particular electrode (including, e.g., whether the electrode is in purely muscle tissue versus in specialized conducting or pacemaking tissue), whether damaged/scarred tissue is in close vicinity to the electrode, depth of the electrode within the tissue, local tissue resistance, presence or absence of any of a large range of local pathologies, etc. Nonetheless, typical anodal phase durations often fall within the range from about two milliseconds to about eight milliseconds, whereas typical cathodal durations often fall within the range from about 0.3 millisecond to about 1.5 millisecond. Typical anodal phase amplitudes (most commonly at the maximum subthreshold amplitude) often fall within the range from about 0.5 volt to 3.5 volts, compared to typical cathodal phase amplitudes from about 3 volts to about 20 volts.

The present invention also permits the physician to readily test ranges of stimulation and other parameters (voltage, duration, shape of voltage versus time pulses, etc.) once the anti-reentry system is in place in the patient. Thus, the ability to engage in trial and error testing of pulsing parameters permits the physician not only to determine such a parameter as maximum subthreshold amplitude, but also to optimize other stimulation parameters to fit a given patient's condition, location of electrodes, etc. Furthermore, the physician may so determine optimal parameters for each individual electrode in a set of multiple electrodes.

Such a system of testing could be related to defibrillation threshold testing, wherein ventricular fibrillation is deliberately provoked and various levels of defibrillatory shocks are given to determine the amount of energy needed. In the present application, testing is done with the various patterns of pacing so as to find the one with the lowest requirement for countershock energy.

Based on the examples provided herein, the skilled practitioner in the art will readily appreciate that generalization of the teachings expands the scope of the present invention to include stimulation time and voltage ranges to beyond those mentioned herein, as well as to beyond the numbers of individual electrodes employed, and other parameters subject to simple and quick experimentation in a specific situation not specifically addressed in the verbiage presented on the practice of the present invention.

Having thus described the basic concept of the invention, it will be readily apparent to those skilled in the art that the foregoing detailed disclosure is intended to be presented by way of example only, and is not limiting. Various alterations, improvements and modifications will occur and are intended to those skilled in the art, but are not expressly stated herein. These modifications, alterations and improvements are intended to be suggested hereby, and within the scope of the invention. Accordingly, the invention is limited only by the following claims and equivalents thereto.

What is claimed is:

1. An apparatus for applying biphasic myocardial stimulation, the apparatus comprising:
  at least two electrodes adapted to administer biphasic stimulation to myocardial tissue; and
  a pacemaker connected to provide biphasic stimulation to the at least two electrodes, wherein the biphasic stimulation comprises:
    a first stimulation phase having a first phase polarity, a first phase amplitude, a first phase shape, and a first phase duration, so as to precondition the myocardium to accept subsequent stimulation, and
    a second stimulation phase having a second phase polarity, a second phase amplitude that is larder in absolute value than the first phase amplitude, a second phase shape, and a second phase duration; and
  wherein the pacemaker repeatedly provides biphasic stimulation so long as fibrillation is detected.

2. The apparatus for applying myocardial stimulation according to claim 1, wherein the first phase polarity is positive, and the second phase polarity is negative.

3. The apparatus for applying myocardial stimulation according to claim 2, wherein the first phase amplitude is at a maximum subthreshold amplitude.

4. The apparatus for applying myocardial stimulation according to claim 3, wherein the maximum subthreshold amplitude is about 0.5 volt to about 3.5 volts.

5. The apparatus for applying myocardial stimulation according to claim 1, wherein the first phase shape is ramped from a baseline value to a second value.

6. The apparatus for applying myocardial stimulation according to claim 5, wherein the second value is not more than a maximum subthreshold amplitude.

7. The apparatus for applying myocardial stimulation according to claim 1, wherein the first phase duration is about one millisecond to about nine milliseconds.

8. The apparatus for applying myocardial stimulation according to claim 1, wherein the second phase amplitude is about two volts to about twenty volts.

9. The apparatus for applying myocardial stimulation according to claim 1, wherein the second phase duration is about 0.2 millisecond to about 1.5 milliseconds.

10. The apparatus for applying myocardial stimulation according to claim 1, wherein the first stimulation phase further comprises a series of stimulating pulses of a predetermined amplitude and duration, and a series of rest periods.

11. The apparatus for applying myocardial stimulation according to claim 10, wherein applying the first stimulation phase further comprises applying a rest period after at least one stimulating pulse.

12. The apparatus for applying myocardial stimulation according to claim 10, wherein the predetermined duration is about 0.2 millisecond to about 1.5 milliseconds.

13. The apparatus for applying myocardial stimulation according to claim 10, wherein the rest period is about 0.2 millisecond to about 1.2 milliseconds.

14. The apparatus for applying myocardial stimulation according to claim 1, wherein the first phase shape is selected from the group consisting of: square wave pulse, ramped pulse, and series of short duration square wave pulses.

15. The apparatus for applying myocardial stimulation according to claim 1, wherein at least one of the electrodes is adapted for application to an inner ventricular wall via the vena cava.

16. The apparatus for applying myocardial stimulation according to claim 1, wherein at least one of the electrodes is adapted for application to an exterior ventricular wall.

17. The apparatus for applying myocardial stimulation according to claim 1, wherein the stimulation is applied to the electrodes progressively in a manner that mimics the normal flow of electrical depolarization in a heart.

18. The apparatus for applying myocardial stimulation according to claim 17, wherein the electrodes closest to the A-V node are the first to administer stimulation, wherein the electrodes farthest from the A-V node, following the normal intrinsic conduction paths, are the last to administer stimulation; and wherein the electrodes intermediate between the electrodes closest to the A-V node and the electrodes farthest from the A-V node each administer stimulation at an intermediate time that is proportional to their intermediate position, following the normal intrinsic conduction paths.

19. The apparatus for applying myocardial stimulation according to claim 18, wherein the electrodes are ordered by class according to their distance from the A-V node, following the normal intrinsic conduction paths.

20. The apparatus for applying myocardial stimulation according to claim 19, wherein the number of classes is between two and about thirty.

21. The apparatus for applying myocardial stimulation according to claim 1, wherein the first stimulation phase comprises an anodal stimulus.

22. A cardiac stimulation apparatus for reverting ventricular arrhythmias with biphasic waveforms, the apparatus comprising:

at least two electrodes adapted to administer biphasic stimulation to cardiac tissue, wherein the biphasic stimulation comprises:

a first stimulation phase having a positive polarity, a subthreshold amplitude, a duration of about one millisecond to about nine milliseconds, and a shape, wherein the shape is selected from the group consisting of: square wave pulse, ramped pulse, and series of short duration square wave pulses; and a second stimulation phase having a negative polarity, an amplitude of about two volts to about twenty volts that is larger in absolute value than the first stimulation chase subthreshold amplitude, and a duration of about 0.2 millisecond to about 1.5 milliseconds.

* * * * *